(12) United States Patent
Jeanne et al.

(10) Patent No.: US 10,687,706 B2
(45) Date of Patent: Jun. 23, 2020

(54) DEVICE AND METHOD FOR OBTAINING AND PROCESSING MEASUREMENT READINGS INCLUDING AT LEAST A COMPONENT REPRESENTATIVE OF A PHYSICAL PHENOMENON IN A LIVING BEING

(75) Inventors: Vincent Jeanne, Eindhoven (NL); Maarten Peter Bodlaender, Eindhoven (NL); Willem Verkruijsse, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 749 days.

(21) Appl. No.: 14/234,454

(22) PCT Filed: Jul. 17, 2012

(86) PCT No.: PCT/IB2012/053645
§ 371 (c)(1),
(2), (4) Date: Jan. 23, 2014

(87) PCT Pub. No.: WO2013/017976
PCT Pub. Date: Feb. 7, 2013

(65) Prior Publication Data
US 2014/0139656 A1     May 22, 2014

Related U.S. Application Data

(60) Provisional application No. 61/513,735, filed on Aug. 1, 2011.

(51) Int. Cl.
*A61B 5/00* (2006.01)
*A61B 5/1455* (2006.01)
(Continued)

(52) U.S. Cl.
CPC .......... *A61B 5/0015* (2013.01); *A61B 5/0077* (2013.01); *A61B 5/021* (2013.01);
(Continued)

(58) Field of Classification Search
CPC .......... A61B 5/0077; A61B 2560/0223; A61B 5/0015; A61B 5/021; A61B 5/024;
(Continued)

(56) References Cited

U.S. PATENT DOCUMENTS 5,891,025 A      4/1999   Buschmann et al.
6,470,199 B1 *  10/2002   Kopotic ............. A61B 5/14552
                                                                    600/310
(Continued)

FOREIGN PATENT DOCUMENTS

EP          0922431          6/1999
EP          1297782 A1       4/2003
(Continued)

OTHER PUBLICATIONS

Allen, J., et al.; Comparison of regional variability in multi-site photoplethysmographic pulse wave characteristics; 2000; First International Conference on Advances in Medical Signal and Information Processing; 26-31.
(Continued)

*Primary Examiner* — Masum Billah
*Assistant Examiner* — Joon Kwon

(57) ABSTRACT

The present invention relates to a device (10) for obtaining and processing measurement readings including at least a component representative of a physical phenomenon in a living being (16), comprising a sensor (12) for obtaining measurement readings from at least one body part of a living being (16) from a distance having at least a component representative of the physical phenomenon in the living being (16), an identification unit (26) for identifying the at
(Continued)

least one body part of the living being (16); an extraction unit (38) for extracting at least one first signal from the measurement readings representing at least one component representative of the physical phenomenon, an evaluation unit (30) for obtaining adjustment information according to the at least one identified body part, and an adjustment unit (34) for adjusting the at least one first signal according to the adjustment information and for generating at least one output signal representing the physical phenomenon of the living being (16).

21 Claims, 5 Drawing Sheets

(51) Int. Cl.
  *A61B 5/021* (2006.01)
  *A61B 5/08* (2006.01)
  *A61B 5/024* (2006.01)
(52) U.S. Cl.
  CPC .......... *A61B 5/024* (2013.01); *A61B 5/02405* (2013.01); *A61B 5/0816* (2013.01); *A61B 5/14551* (2013.01); *A61B 5/4821* (2013.01); *A61B 2560/0223* (2013.01)
(58) Field of Classification Search
  CPC .............. A61B 5/02405; A61B 5/0816; A61B 5/14551; A61B 5/4821
  USPC ........................................ 340/870.01; 348/77
  See application file for complete search history.

(56) References Cited

U.S. PATENT DOCUMENTS

| | | | |
|---|---|---|---|
| 9,301,697 B2* | 4/2016 | Baker, Jr. | A61B 5/021 |
| 2003/0176776 A1* | 9/2003 | Huiku | A61B 5/1495 |
| | | | 600/322 |
| 2008/0221410 A1* | 9/2008 | Campbell | A61B 5/0059 |
| | | | 600/310 |
| 2009/0082681 A1* | 3/2009 | Yokoyama | A61B 5/024 |
| | | | 600/509 |
| 2009/0296991 A1* | 12/2009 | Anzola | G06F 3/011 |
| | | | 382/107 |
| 2011/0311119 A1* | 12/2011 | Jeanne | G06T 7/20 |
| | | | 382/128 |
| 2012/0195473 A1* | 8/2012 | De Haan | G06T 7/20 |
| | | | 382/107 |
| 2012/0226168 A1* | 9/2012 | Osorio | A61B 5/0205 |
| | | | 600/484 |
| 2013/0245462 A1* | 9/2013 | Capdevila | A61B 5/02405 |
| | | | 600/479 |

FOREIGN PATENT DOCUMENTS

| | | |
|---|---|---|
| EP | 1665988 | 6/2006 |
| WO | 2006070823 | 7/2006 |
| WO | 2007063516 A2 | 6/2007 |
| WO | 2011042851 A1 | 4/2011 |
| WO | 2011042858 A1 | 4/2011 |

OTHER PUBLICATIONS

Humphreys, K., et al.; Noncontact simultaneous dual wavelength photoplethysmography: A further step toward noncontact pulse oximetry; 2007; Review of Scientific Instruments; 78:044304.

Humphreys, K. G.; An Investigation of Remote Non-Contact Photoplethysmography and Pulse Oximetry; 2007; Thesis submitted to the National University of Ireland.

Kalal, Z., et al.; Online learning of robust object detectors during unstable tracking; 2009; IEEE 3rd On-line Learning for Computer Vision Workshop—Kyoto, Japan.

Verkruysse, W., et al.; Remote plethysmographic imaging using ambient light; 2008; Optics Express; 16(26) 21434-21445.

\* cited by examiner

DEVICE AND METHOD FOR OBTAINING AND PROCESSING MEASUREMENT READINGS INCLUDING AT LEAST A COMPONENT REPRESENTATIVE OF A PHYSICAL PHENOMENON IN A LIVING BEING

CROSS REFERENCE TO RELATED APPLICATIONS

This application is a national filing of PCT application Serial No. PCT/IB2012/053645, filed Jul. 17, 2012, published as WO 2013/017976 A1 on Feb. 7, 2013, which claims the benefit of U.S. provisional application Ser. No. 61/513,735 filed Aug. 1, 2011, which is incorporated herein by reference.

FIELD OF THE INVENTION

The present invention relates to a device and a method for obtaining and processing measurement readings including at least a component representative of a physical phenomenon in a living being. The invention also relates to a computer program for implementing said method.

BACKGROUND OF THE INVENTION

Traditional sensors for measuring a physical phenomenon, like a blood oxygenation, are usually designed for direct use on a single body-part. For example the sensors are designed as finger-clips, ear-clips, forehead-sensors, toe-clips or ankle-sensors comprising infrared light sources and infrared detectors. These sensors are shaped such that they fit perfectly on the according body-part. Each body part has different light reflection and/or light transmission characteristics due to the inner structure of the skin, for example the skin is thicker on feet than on face leading to higher amplitude of measurements of the physical phenomenon on the face then on the feet. To overcome these differences, predetermined calibration curves are used, wherein the calibration curves are adapted for the body-part on which the measurement is taken. The correct calibration curve can be selected easily for the sensors described above, since the sensors are clearly dedicated to a specified body part. After selecting the correct calibration curve, the measured values are calculated from a raw signal obtained by the traditional sensor using the selected calibration curve.

In camera-based vital signs monitoring physical phenomena can be measured unobtrusively from a distance. A problem is that in camera-based vital signs monitoring it cannot be concluded from different sensor designs which body part is actually measured. Hence, specific calibration curves cannot be selected directly. However, a body part independent adjustment does not yield the accuracy required by healthcare professionals.

SUMMARY OF THE INVENTION

It is an object of the present invention to provide a method, a device and a computer program of the types mentioned above enabling measuring a physical phenomenon of a living being from a distance and outputting an accurate output signal representing the physical phenomenon of the living being.

In a first aspect of the present invention a device is presented for obtaining and processing measurement readings including at least a component representative of a physical phenomenon in a living being, including a sensor for obtaining measurement readings from at least one body part of a living being from a distance having at least a component representative of the physical phenomenon in the living being, an identification unit for identifying the at least one body part of the living being, an extraction unit for extracting at least one first signal from the measurement readings representing at least one component representative of the physical phenomenon, an evaluation unit for obtaining adjustment information according to the at least one identified body part, and an adjustment unit for adjusting the at least one first signal according to the adjustment information and for generating at least one output signal representing the physical phenomenon of the living being.

In a further aspect of the present invention a method is presented for obtaining and processing measurement readings including at least a component representative of a physical phenomenon in a living being, including the steps of obtaining measurement readings from at least one body part of a living being from a distance having at least a component representative of the physical phenomenon in the living being, identifying the at least one body part of the living being, extracting at least one first signal from the measurement readings representing at least one component representative of the physical phenomenon, obtaining adjustment information according to the at least one identified body part, adjusting the at least one first signal according to the adjustment information, and generating at least one output signal representing the physical phenomenon of the living being.

In a further aspect of the present invention a processor is presented for processing measurement readings including at least a component representative of a physical phenomenon in a living being, including an interface for receiving measurement readings from at least one body part of a living being obtained from a distance and having at least a component representative of the physical phenomenon in the living being, an identification unit for identifying the at least one body part of the living being, an extraction unit for extracting at least one first signal from the measurement readings representing at least one component representative of the physical phenomenon, an evaluation unit for obtaining adjustment information according to the at least one identified body part and an adjustment unit for adjusting the at least one first signal according to the adjustment information and for generating at least one output signal representing the physical phenomenon of the living being.

In a further aspect of the present invention a method is presented for processing measurement readings including at least a component representative of a physical phenomenon in a living being, including the steps of receiving measurement readings from at least one body part of a living being obtained from a distance and having at least a component representative of the physical phenomenon in the living being, identifying the at least one body part of the living being, extracting at least one first signal from the measurement readings representing at least one component representative of the physical phenomenon, obtaining adjustment information according to the at least one identified body part, adjusting the at least one first signal according to the adjustment information, and generating at least one output signal representing the physical phenomenon of the living being.

In a further aspect of the present invention a computer program is presented comprising program code means for causing a computer to carry out the steps of the method described above when said computer program is carried out on the computer.

The invention is based on the idea to identify body parts from the measurement readings obtained by the sensor from a distance. Based on the identified body parts adapted adjustment information can be selected and applied to corresponding signals to provide an accurate output signal.

The sensor is obtaining the measurement readings from a distance to the living being. The sensor can be for example an image sensor. Generally, any kind of sensor can be used that provides measurement readings, in particular image data, from which the at least one first signal can be extracted. Further, a plurality of sensors may be used for obtaining measurement readings. For instance, different units, e.g. the identification unit and the extraction unit, may receive measurement readings from different sensors. Different sensors can also differ in their position and/or their specifications. For instance, they can be used for obtaining measurement readings from different angles and/or with different wavelength of light. In this way, more information is provided for examining the living being so that the accuracy of the examination can be improved. Thus, the measurement readings can be obtained very easily and without discomfort for the living being. Under the term living being preferably a human being, e.g. a patient, is understood. Alternatively, the invention can be used with other living beings like animals. Further, since the sensor is generally not attached to the body of the living being there is no need for a body-part specific shape of the sensor. Therefore, it is not directly known from the type of the sensor what part of the body is actually measured. More important, by obtaining the measurement readings from a distance the measurement readings can be obtained from a plurality of body parts simultaneously, leading to a plurality of component representatives of the physical phenomenon included in the measurement readings. Preferred body parts are face, arms, legs, hands, feet, palm, fingers and/or toes.

The identification unit identifies the at least one body part of which the measurement readings are taken. It can generate at least one identification data label defining the identified body part for further use.

This can, for instance, be achieved by using object detection techniques for image giving sensors to detect and select one or more body parts based on the measurement readings. A suitable body part detector for image giving sensors is described in "Robust Real-time Object Detection", Viola, Paul; Jones, Michael; Vancouver, Canada, 2001. A visual object detection framework is described that is capable of processing images rapidly while achieving high detection rates. This is based on an image representation called an "Integral Image" allowing a quick computing. Further, a learning algorithm is used which selects a small number of critical visual features and yields efficient classifiers. Finally, the classifiers are combined in a "cascade" which allows background regions of the image to be discarded. This algorithm is in particular suitable for detecting a face of a human as the part of the body.

In an embodiment the body part identification can be implemented based on heuristics. Thereby image processing techniques can be used, like edge detection and color segmentation.

In a further embodiment the body part identification is based on three-dimensional information of the body. The three-dimensional information can be obtained separately, for example by a 3D-camera or by a stereo vision system. Alternatively, the sensor can be designed as a 3D-camera or as a stereo vision system.

In a still further embodiment a set of pre-trained body part detectors is used for identifying the body parts. Each detector is trained for identifying a specific body part, e.g. face, hand, arm or foot. When the measurement readings are examined by the body part detectors the label is created by the object detector giving the highest response. When images are obtained as measurement readings the body part detectors can examine the image in sections and assign labels to each section individually.

In a still further embodiment, the body part detection is applied using a manual initialization by a user and an online learning body part detection approach. Such an approach is described in "Online learning of robust object detectors during unstable tracking", Kalal et al, Kyoto, Japan, 2009. Online learning body part detection has the advantage of being able to provide detections that are tailored to the current environment, e.g. lighting conditions, and the body part being measured, e.g. body-part deformations.

To further improve identifying body parts, context information can also be taken into account by the identification unit. For example, body models can be used as context information. Based on the context model false identifications can be removed, e.g. a foot can never be attached to a head.

The proposed extraction unit extracts the at least one first signal from the measurement readings. The at least one first signal is a representative for the physical phenomenon to be measured. It is preferably related to one measurement point at one body part of the living being. Extracting the at least one first signal from the measurement readings is preferably done based on information given by the body parts identified as described above. For example, the extracting can be achieved by at least one of the methods described in "Non-contact simultaneous dual wavelength photoplethysmography: A further step toward noncontact pulse oximetry", Humphreys et al, Review of scientific instruments 78, 2007; or "Pulse Oxigraphy—And other new in-depth perspectives through the near infrared window", Wieringa, 2007. As a result, a single first signal or a plurality of first signals is extracted.

Further, the evaluation unit is obtaining adjustment information based on the body parts identified by the identification unit. The adjustment information is preferably predetermined information. It can be stored in data storage means of the device. In this case the evaluation unit is reading the adjustment information from this data storage means according to the labels defined by the identified body parts.

The adjustment unit is adjusting the at least one first signal based on the adjustment information received from the evaluation unit. If only one first signal is extracted or only one first signal is used, the output signal is directly generated by adjusting the first signal. If a plurality of first signals is identified, those first signals are adjusted separately using according adjustment information.

It is preferred to implement the identification unit, the extracting unit, the evaluation unit and the adjustment unit as one or more microprocessor(s), e.g. as a personal computer or workstation.

The invention therefore provides a device and a method which allows generating a highly accurate output signal representing the physical phenomenon of the living being.

Preferred embodiments of the invention are defined in the dependent claims. It shall be understood that the claimed method has similar and/or identical preferred embodiments as the claimed device and as defined in the dependent claims.

In an embodiment of the invention the physical phenomenon is blood oxygenation, pulse, blood pressure, heart rate variability, respiratory rate, depth of anesthesia and/or hypo- and hypervolemia, i.e. the device and method according to the present invention are generally able to derive corresponding vital signs (also called biometrical signals). In this embodiment at least one specific physical phenomenon is measured. Depending on the physical phenomenon to be measured different extraction techniques have to be provided. As for example pulse, heart rate variability and respiratory rate are periodical phenomena. These phenomena can be extracted by extraction techniques for periodic changes in the measurement readings. The phenomena blood oxygenation and blood pressure are not necessarily of a periodic kind. Hence, a more static extraction technique is needed. It is advantageous that the invention provides a single way for correcting first signals for these different kinds of measured physical phenomena based on the same concept. It is further advantageous, that multiple phenomena can be measured with the same device by replacing the extraction technique and/or providing multiple extraction techniques in a parallel manner. This is leading to a very economical device and method.

In a further embodiment the sensor is a video camera. In this embodiment a video camera, is used for obtaining the measurement readings. Hence, the measurement readings are a sequence of images. The video camera can be a digital video camera of a traditional kind. It is possible to obtain measurement readings from the entire visible spectrum of light. Alternatively, the video camera can be adapted to a narrower band of wavelengths or to specific wavelengths that are relevant for the physical phenomenon to be measured, as for example an infrared camera or an RGB camera. As for example, if blood oxygenation should be measured a combination of the green, red and infrared wavelength band is of main interest.

A further alternative for an adapted video camera is a terahertz camera. The terahertz camera is adapted to an electromagnetic spectrum which is located between microwaves and near-infrared regions of the electromagnetic spectrum. This specific camera has the advantage of measuring through different types of material, as for example clothes. Further, it is measuring more deeply through skin and is less sensitive to motions of the examined living being. Therefore, the terahertz camera provides a very robust way for obtaining high quality measurement readings. In addition, depending on the application, an additional light source including the wavelengths used for the desired measurement can be used to improve the measurement readings. It is an advantage that such video cameras are highly available and very cost effective. A further advantage is that the measurement readings obtained by the video camera contain a plurality of information which can be analyzed over time as to identify the body parts correctly and to adapt to changes in a determined scene, e.g. to light conditions.

In a further embodiment the adjustment information is at least one calibration curve. In this embodiment each first signal is adjusted based on an according predetermined calibrations curve. The calibration curve is assigned to the identified body part and stored in the data storage means. After a body part has been identified the label describing the according body part is received by the evaluation unit. The evaluation unit can then read out the according calibration curve from data storage means comprising a dataset of predetermined calibration curves. It is an advantage that calibration curves are providing different adjustment values related to different values of the first signal. This is leading to a more exact adjustment of the at least one first signal. Further, it can be intended to adapt the calibration curve according to the living being examined. For example, the calibration curve can be adapted manually by comparing the output signal with a measurement of the physical phenomenon from another measurement device. Therefore, a very exact adjusted at least one first signal can be generated. Further, the usage of a predetermined calibration curve advantageously provides the possibility of establishing real-time calibration, since they are available and applicable very fast.

In a further embodiment the extracting unit is adapted for extracting the at least one first signal from the measurement readings according to the at least one identified body part. In this embodiment the at least first signal is extracted based on the information obtained by the identification unit. The information of the identified body part can be used to accurately extract the at least one first signal. For example, if an arm has been identified in an image obtained by the sensor, the signal can be extracted only from the region of the image, where the arm is assumed. Further, the information of the region can be used in following images obtained by the sensor. This applies for a plurality of identified body parts. Therefore, the rest of the image not representing any body parts can be discarded preventing the first signal respectively the first signals from artifacts. An advantage is that the at least one first signal can be extracted very accurately. Further, this embodiment improves robustness of the extraction.

In a further embodiment the identification unit is adapted for estimating motions of the at least one identified body part and the extraction unit is adapted for extracting the at least one first signal in accordance with the estimated motions. In this embodiment motions of the living being are taken into account for identifying body parts and extracting the at least one first signal. Motions of the living being to be examined can lead to unclear measurement readings. After identifying the body part, its movements can be tracked to adapt the extraction. Therefore, a qualitatively better at least one first signal is obtained, wherein artifacts are reduced. Further, it is thinkable to track the whole movement of the living being for an overall motion robust implementation of the method. For example, general motion compensation can be implemented. Alternatively or additionally, it could be estimated based on a body model if a previously identified body part will be moved out of a sensor area by the estimated motions and/or if another body part is moved into the sensor area by the estimated motions.

Further, the identification unit can be adapted for identifying a posture of the at least one identified body part. The posture of the body parts may affect the measurement readings. By identifying the posture, additional information can be taken into account by the extraction unit, the evaluation unit and/or the adjustment unit. The additional information can for example relate to lighting conditions at the body part affected by its posture or to overlapping body parts, wherein regions of one body part is covered by another body part. The posture can be described for example by a three-dimensional model of at least one body part of the living being.

In a further embodiment an analyzing unit is provided for comparing at least two first signals representing component representatives of the physical phenomenon from different body parts of the living being. In this embodiment the possibility of measuring multiple body parts at the same time is additionally used. It is physically normal to obtain different measurement readings from different body parts of one living being. However, after adjusting the first signals of different body parts, the first signals should correspond approximately to each other. By comparing the first signals after adjusting them, additional information about the living being can be obtained. If for example substantially different first signals are obtained from different legs, it can be assumed that a pathological difference is present, e.g. based on a thrombosis.

In a further embodiment the analyzing unit is adapted for determining a difference between the at least two first signals and for generating a reporting signal if the difference exceeds a threshold. In this embodiment the adjusted first signals from different body parts are compared by computing their difference. If the difference between the signals exceeds a predetermined threshold an abnormality is assumed and a reporting signal is generated. The reporting signal can e.g. be an acoustic or an optic signal reporting a presence of the abnormality to a user. Further, it is preferred if the according body parts are also reported to the user by the reporting signal. Hence, a user of the device is informed that an abnormality is eventually present and where this abnormality is assumed. The user can examine the living being very quickly based on this information. It is further preferred if different thresholds are used which are adapted to different pairings of first signals of different body parts leading to a higher accuracy of the reporting signal.

In a further embodiment the adjustment unit is adapted for generating the output signal based on at least two first signals. In this embodiment the output signal is generated in accordance to a plurality of adjusted first signals. One of the major advantages of the inventive idea is that a plurality of first signals can be obtained which should be substantially identical after adjusting. By selecting adjusted first signals and/or combining them, the output signal can be generated with especially high accuracy. A selection can be made e.g. by discarding first signals from body parts which are not suitable for obtaining measurement readings.

In a further embodiment the adjustment unit is adapted for determining a quality of the at least two first signals and for selecting at least one first signal based on the quality. In this embodiment a quality of the at least two first signals and/or adjusted first signals is determined to select at least one suitable adjusted first signal for generating the output signal. The quality can be estimated for example from a noise to signal ratio, from a time the according body part could be obtained by the sensor, from an amount of motion detected in the body part being monitored, an amount of gradient, an amount of colour variation and/or a light level of the body part being monitored. It is thinkable to generate the output signal by selecting the one adjusted first signal comprising the highest quality. It is an advantage that the output signal is based on at least one first signal with the highest quality available, leading to a very high quality of the output signal.

In a further embodiment the adjustment unit is adapted for merging the at least two first signals for generating the output signal. In this embodiment the output signal is generated based on at least two first signals. It is preferred to merge adjusted first signals according to different body parts. Hence, a very accurate output signal is generated. Additionally, the first signals can be selected according to a minimum quality, wherein only adjusted first signals are merged comprising a minimum quality. Further, it is advantageous to apply a phase-shift to the adjusted first signals specific to the according body parts. As for example, a pulsation measured at an arm will be slightly ahead of the same pulsation measured at a foot for different distances to the heart leading to different pulse transit times. The adjusted first signals can be merged in different ways. They can be merged for example by arithmetical averaging. This is leading to a very fast approach which can be computed easily. Further, a weighted averaging is thinkable. The weighting can be made e.g. by using quality factors according to the quality of the at least one first signal.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
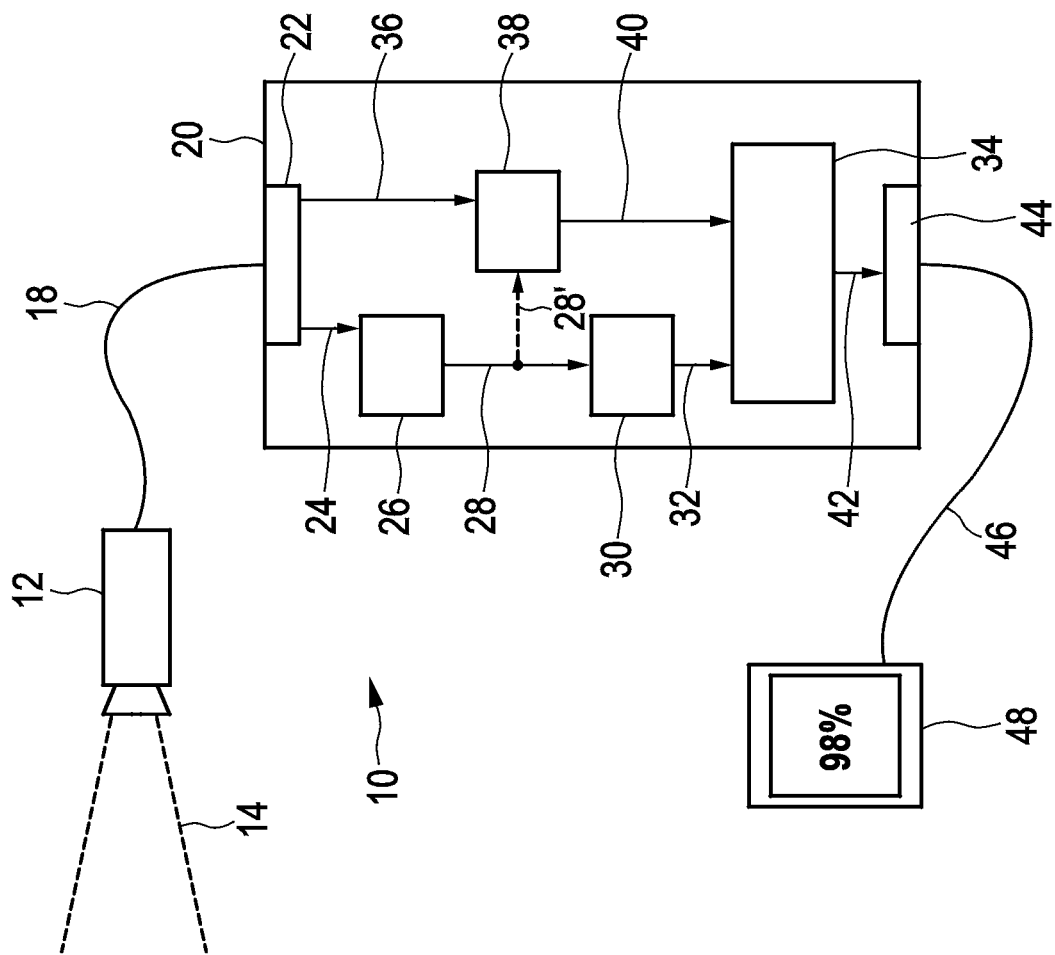
FIG. 1 shows a schematic of a first embodiment of a device according to the invention.
Figure 1:
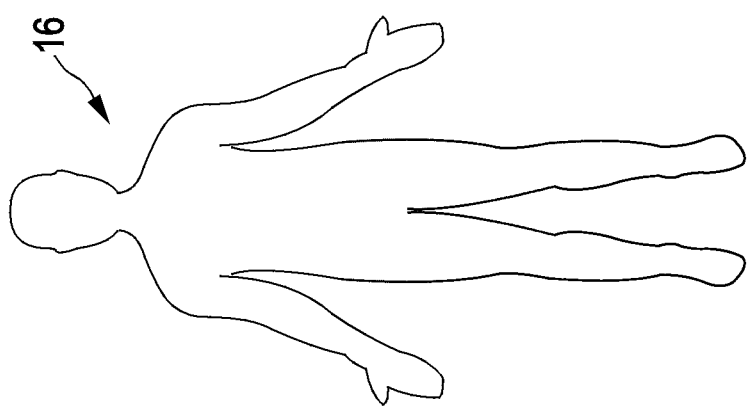

FIG. 1 shows a first embodiment of a device 10 according to the present invention. The device 10 comprises a video camera 12 as a sensor. The video camera 12 has a sensor area 14 wherein it can obtain measurement readings from a human being 16. The sensor area 14 can include the whole human being 16 or only parts of the human being 16. The measurement readings obtained by the video camera 14 are in the form of a sequence of images having a component representative of a physical phenomenon of the human being. In the following the invention is exemplarily described with a blood oxygenation as the physical phenomenon to be measured. It has to be understood that this does not limit the invention. Other physical phenomena which can be advantageously be measured by the invention are e.g. pulse, heart rate variability, blood pressure, respiratory rate, depth of anesthesia and/or hypo- and hypervolemia. The sequence of images is transmitted via a line 18 to a processor 20 of the device 10.

The processor 20 comprises an interface 22 for receiving the measurement readings. In the processor 20 the measurement readings are transmitted via an arrow 24 to an identification unit 26. The identification unit 26 is analyzing the measurement readings for identifying at least one body part of the human being 16 suitable for measuring the physical phenomenon. The body part can be for example face, arm, hand, leg, foot, toe and/or thumb. The identifying is accomplished by an object detecting algorithm executed within the identification unit 10 for detecting body parts in images. After indentifying the at least one body part, the identification unit 26 is generating data labels with information which at least one body part has been identified, e.g. "right toe". This information is transmitted via an arrow 28 to an evaluation unit 30. The evaluation unit 30 comprises data storage means, wherein calibration curves are stored. Based on the information send by the identification unit 26, the evaluation unit 30 is selecting according calibration curves from the data storage means and transmitting those via an arrow 32 to an adjustment unit 34.

Starting again from the interface 22, the measurement readings are also transmitted via an arrow 36 to an extraction unit 38. The extraction unit 38 is extracting at least one first signal from the measurement readings received. Since the measurement readings are images this is accomplished by using image processing algorithms. As for example it can be desired to first locate suitable measurement spots in the images, preferably by searching skin-colored pixels. Then these measurement spots are analyzed for extracting the at least first signal. In the case of blood oxygenation, the color of the skin is evaluated as to obtain a series of values for the blood oxygenation. As shown in FIG. 1 information about the identified body parts can be optionally transmitted via an arrow 28' to the extraction unit 38. The extraction unit 38 can use this information to enhance the quality of the extracted at least one first signal. In particular, the identification unit 26 can identify the at least one region in the sequence of images wherein the at least one body part to be measured is located. This region is transmitted to the extraction unit 38, e.g. as a "mask", defining the areas, where the extraction unit 38 has to extract the according first signal. Hence, the first signal extracted based on this information can be easily linked to the according calibration curve from the evaluation unit 30. After extracting the at least one first signal, it is transmitted via an arrow 40 to the adjustment unit 34. In the adjustment unit 34 each first signal is adjusted according to the assigned calibration curve selected by the evaluation unit 30. Each calibration curve is assigned to its according first signal based on the body part they are related to. Then the calibration curve is applied with the according first signal generating an adjusted first signal.

If only one adjusted first signal is generated, the adjustment unit is outputting the adjusted first signal as an output signal. If a plurality of adjusted first signals is generated the adjustment unit 34 generates the output signal based on the plurality of adjusted first signals. This is done by selecting and/or merging adjusted first signals.

The output signal is transmitted via an arrow 42 to an output interface 44. The output interface 44 is connected with a line 46 transmitting the output signal to a display 48. The display 48 is displaying the value of the output signal representing the physical phenomenon. In this case a blood oxygenation of 98%.

Figure 2:
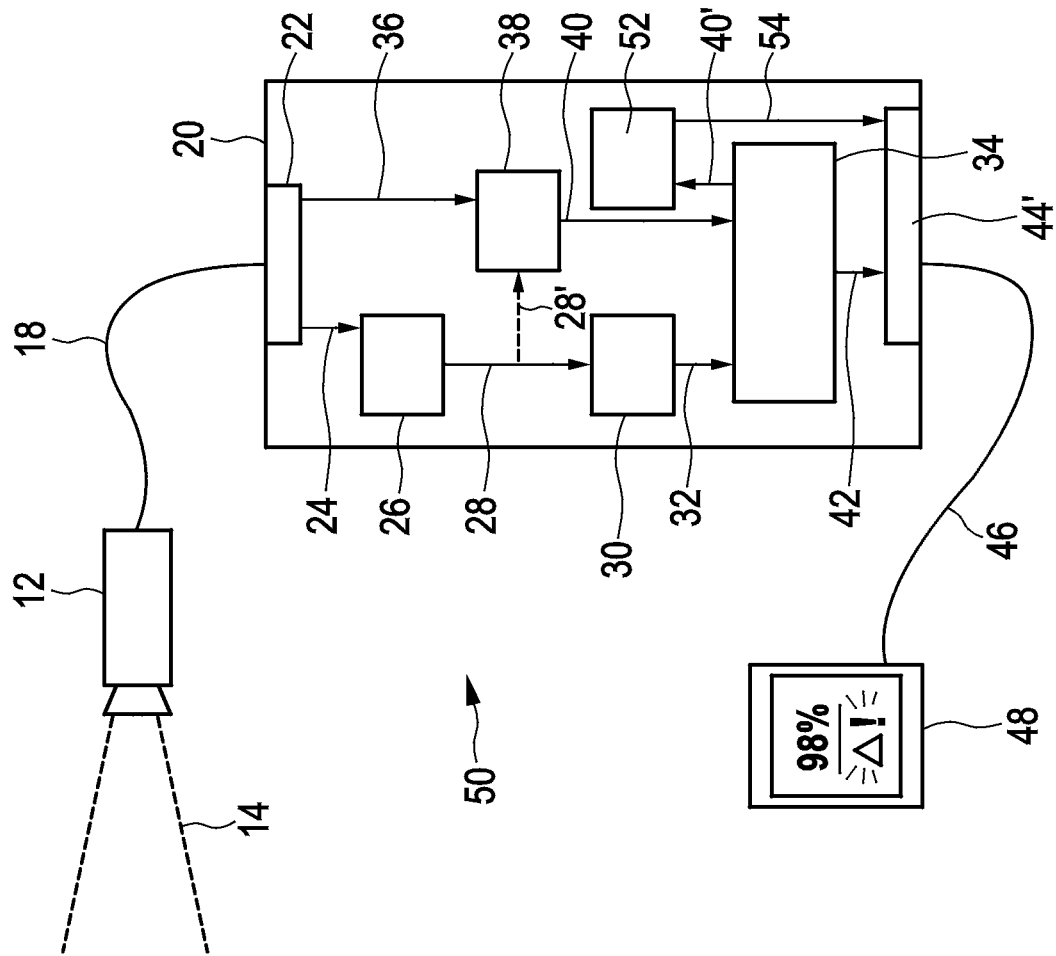
FIG. 2 shows a schematic of a second embodiment of a device according to the invention comprising an analyzing unit.
Figure 2:
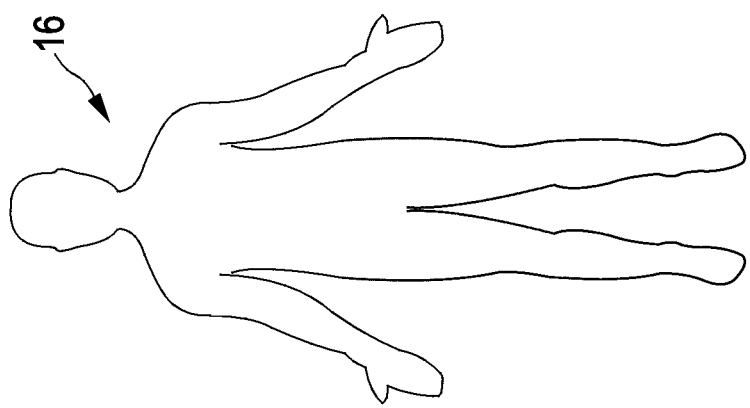

FIG. 2 shows a second embodiment of a device 50 according to the present invention. The device 50 comprises the same components as the device 10 of FIG. 1. Additionally, the device 50 comprises an analyzing unit 52. The analyzing unit 52 is receiving the adjusted at least one first signal via an arrow 40'. If a plurality of adjusted first signals is transmitted, the adjusted first signals are compared to each other by calculating their difference. Preferably this is accomplished in pairs of adjusted first signals, wherein each first signal represents the physical phenomenon in a different body part. Further, the differences calculated are compared to a threshold. The threshold is a predetermined threshold and is stored in data storage means of the analyzing unit 52. If at least one of the differences exceeds the threshold, a reporting signal is generated. The reporting signal is transmitted to an output interface 44' via an arrow 54. The output interface 44' is outputting the reporting signal additionally to the output signal via the line 46 to the display 48. Based on the reporting signal, the display 48 is displaying additional information, indicating a raised difference between at least two of adjusted first signals.

Figure 3:
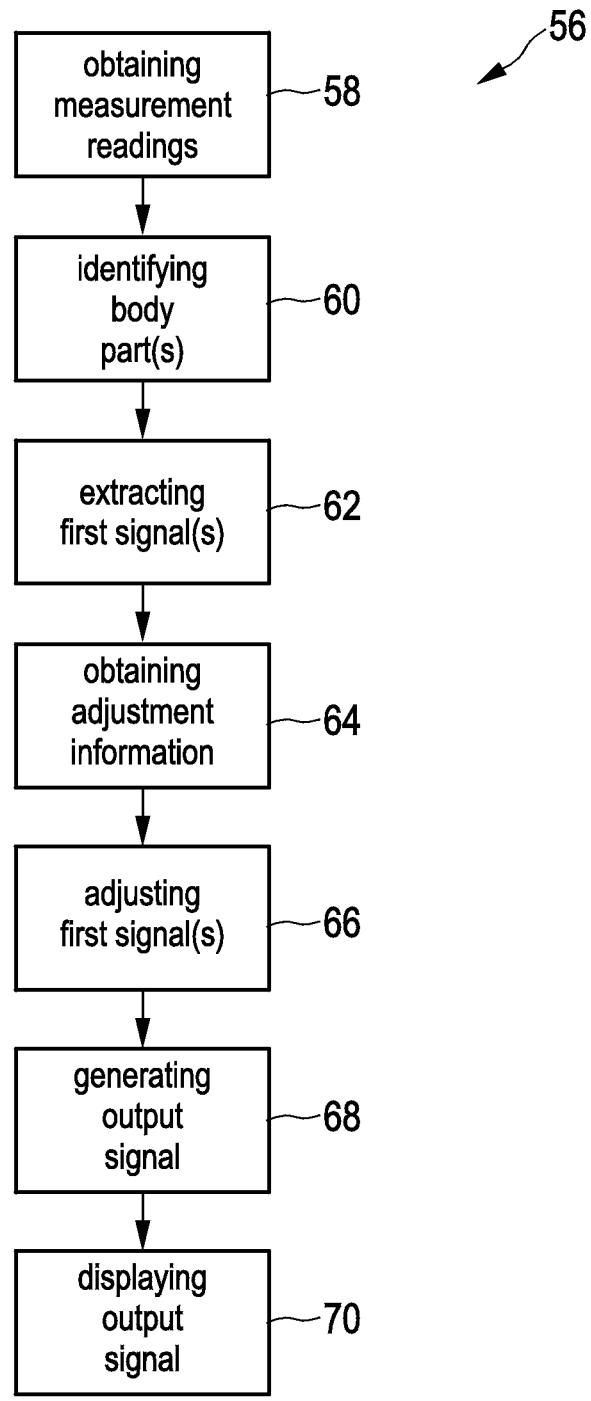
FIG. 3 shows a flow chart illustrating a first embodiment of a method according to invention.

FIG. 3 shows a flow chart 56 of a first embodiment of a method according to the present invention. The steps of flow chart 56 will be explained with respect to the embodiment of the device 10 shown in FIG. 1.

The method begins in a first step 58. In step 58 measurement readings are obtained. As shown in FIG. 1 the measurement readings are obtained by the video camera 12 as a sequence of images. These images are then transmitted to the processor 20.

In a following step 60 at least one body part of the observed living being is identified. The identification unit 26 is carrying out this step 60. As the measurement readings are images, the identifying can be accomplished by image processing algorithms, as for example object recognition algorithms. The gained information regarding body parts can be the existence of a specific body part in the images, a location of a body part in the images, motion information of the body part and the specific type of the body part. The information is then provided for further steps in the method.

In a further step 62 the at least one first signal is extracted from the sequence of images. The number of first signals depends on the number of measurement points in the images. It is possible to extract only one overall first signal based on the images. However, it is preferred to extract at least one first signal for each identified body part to provide as many first signals from different measuring points as possible. The information about the location of body parts in the images obtained in step 60 can be used to define the measurement points within the images.

In a further step 64 adjustment information is obtained. In this step the evaluation unit 30 is using the information about which at least one body part is indentified to select at least one according calibration curve from the data storage means. Hence, for each identified body part an according first signal and an according calibration curve is provided.

In a further step 66 the at least one first signal is adjusted. In this step the adjustment unit 34 is receiving the at least one calibration curve obtained in step 64 and the at least one first signal obtained in step 62. The calibration curve is applied to the according first signal based on the body part they are assigned to wherein at least one adjusted first signal is generated.

In a further step 68 an output signal is generated based on the at least one adjusted first signal. If only one adjusted first signal is received this one adjusted first signal is used as the output signal directly. If a plurality of adjusted first signals is present the output signal is generated based on a selection of at least one of the adjusted first signals and/or based on merging of at least two adjusted first signals. A selection can be realized by determining a quality of each first signal or adjusted first signal. The quality can be determined by known techniques based on a noise to signal ratio, from a time the according body part could be obtained by the video camera, from an amount of motion detected in the body part being monitored, from an amount of gradient, from an amount of colour variation and/or from a light level of the body part being monitored. Based on the quality at least one first signal is selected which is used as output signal. If no selection is done or if a plurality of adjusted first signals remains after the selection, the remaining adjusted first signals are merged to generate a single output signal. By merging a plurality of adjusted first signals a very exact output signal is generated, which is based on combined readings from a plurality of body parts examined. Additionally, the merging has the advantage that if the living being is moving relative to the video camera the one output signal can be generated internally based on changing body parts in the obtained images leading to stable value to be outputted. Hence, the merging leads to a very robust approach. The merging can be done by techniques as an arithmetic averaging or a weighted averaging. The weighted averaging can be weighted based on quality parameters determined for the selection described above. Additionally, the adjusted first signals are shifted in their phase as to provide a common phase since a phase shift of the physical phenomenon arises between different body parts for the body structure of living beings. The shifting can be made according to predetermined shifting values or by fitting minima and maxima of periodical first signals with respect to each other.

In a further step 70 the output signal is displayed to a user. In this step the output signals is received by the display 48 which displays a value according to the physical phenomenon measured and according to the output signal.

The steps 58 to 70 are preferably repeated as to provide a continuous value displayed to the user.

Figure 4:
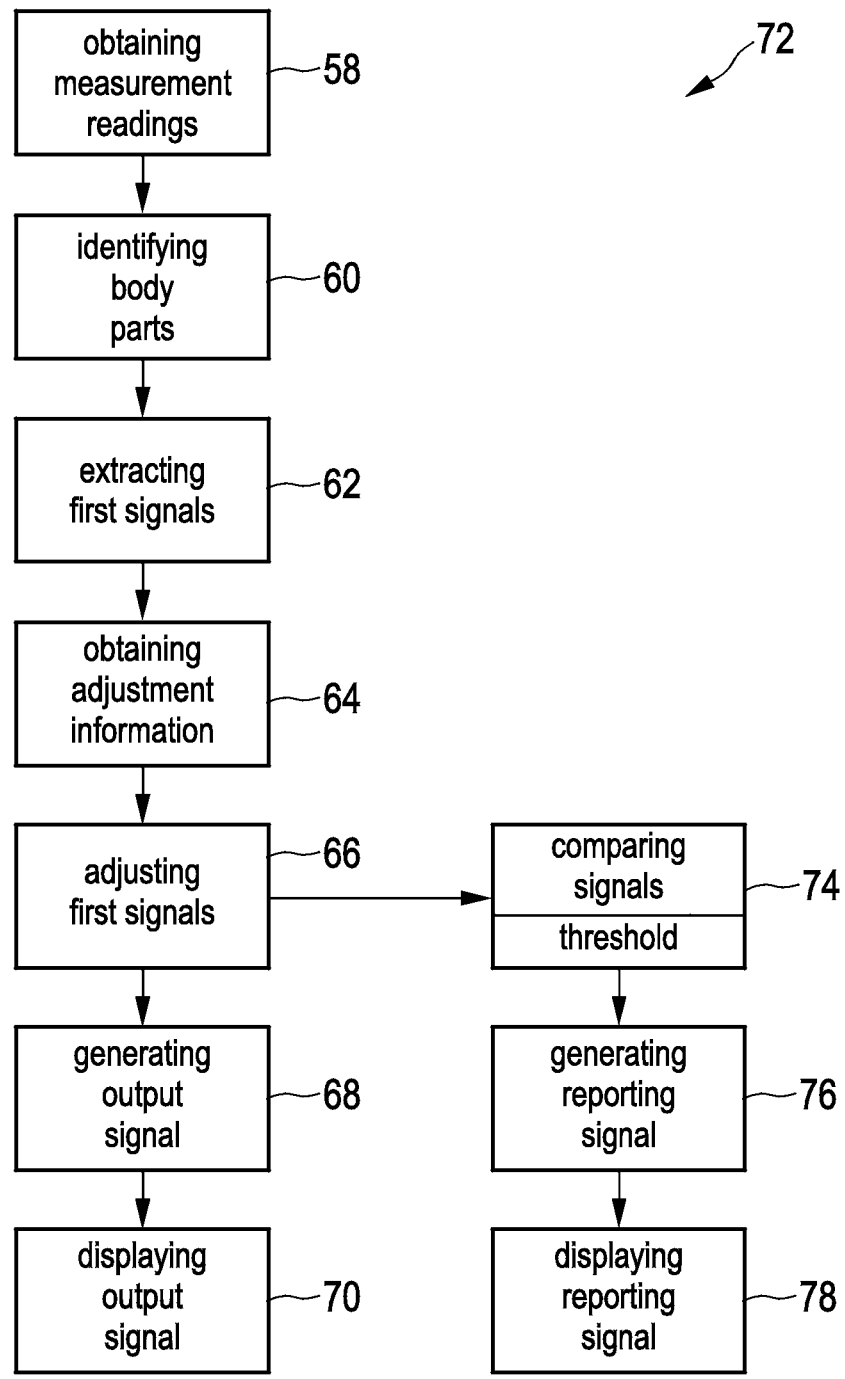
FIG. 4 shows a flow chart illustrating a second embodiment of a method according to invention.

FIG. 4 shows a flow chart 72 of a second embodiment of a method according to the present invention. The flow chart 72 comprises the steps 58 to 70 from flow chart 56 of FIG. 3. The additional steps of flow chart 72 will be explained with respect to the embodiment of the device 50 shown in FIG. 2.

Coming from step 66 in step 74 a plurality of adjusted first signals are compared to each other. This is made by calculating the difference between two adjusted first signals. By cross referencing different pairings of adjusted first signals different differences will be calculated. Each difference is compared to a predetermined threshold which is read out of data storing means. It is preferred if different pairings of adjusted first signals are determined with a threshold adapted to this specific pairing. Therefore, the data storage means stores a plurality of thresholds which are assigned to different pairings adjusted first signals from different body parts. Hence, a selective surveillance of the adjusted first signals is gained.

If at least one difference is exceeding the according threshold a reporting signal is generated in step 76. The reporting signal is then displayed in a further step 78 to a user. It is informing the user of the unusual high difference which could suggest a physical problem. It is preferred if the reporting signal is also reporting to which body parts it is referred to inform the user at which body parts he should examine first.

Figure 5:
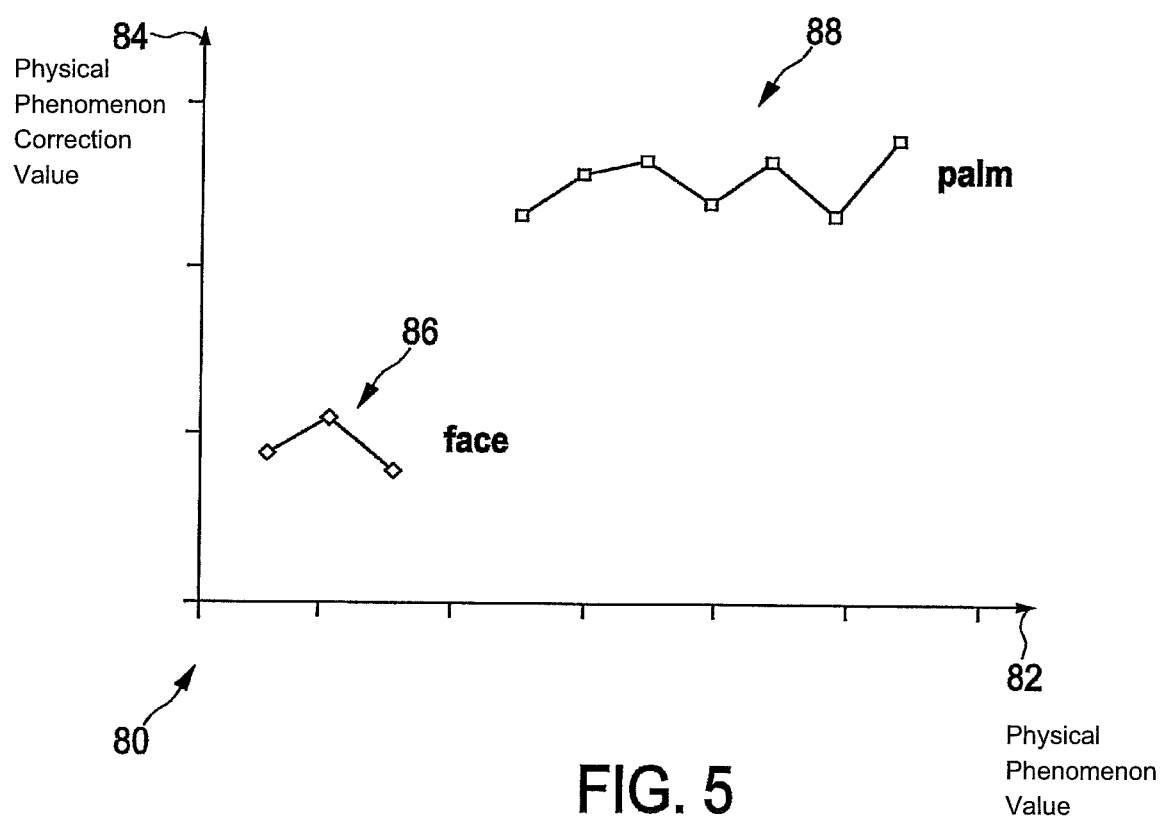
FIG. 5 shows a diagram illustrating adjustment information for different body parts.

FIG. 5 shows a diagram 80 having an abscissa 82 describing the value of the physical phenomenon and an ordinate 84 describing a correction value for the physical phenomenon. In the diagram a first group 86 of three calibration values is shown which is related to a first signal determined of a face of the living being as a body part. Further, a second group 88 of seven calibration values is shown which is related to a first signal determined of a palm of the living being as a body part. The calibration values of each group 86, 88 can be interconnected by interpolation as to form calibration curves for different body parts providing detailed calibration information within an interval. The evaluation unit 30 is selecting one of the calibration curves respectively groups of calibration values 86 or 88 according to the body part identified by the identification unit 26. The adjustment unit 34 is then determining the actual calibration value to apply based on the calibration curve and the value of the first signal to be adjusted. Finally, the adjustment unit 30 is adding the actual calibration value to the according value of the first signal as to adjust the signal.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for obtaining and processing measurement readings including at least a component representative of a physical phenomenon in a living being, comprising:
    a sensor configured to obtain measurement readings from at least one body part of a living being from a distance having at least a component representative of the physical phenomenon in the living being;
    at least one processor programmed to:
        identify the at least one body part of the living being from the obtained measurement readings;
        extract at least one first signal from the measurement readings representing at least one component representative of the physical phenomenon;
        obtain at least one calibration curve corresponding to the at least one identified body part, the at least one calibration curve including calibration values corresponding to first signal values of the at least one first signal;
        adjust the at least one first signal by adjusting the first signal values of the at least one first signal to correspond with the corresponding calibration values of the at least one calibration curve; and
        generate at least one output signal representing the physical phenomenon of the living being by processing the calibration curve and the adjusted at least one first signal with the adjusted first signal values.

2. The device according to claim 1, wherein the physical phenomenon is blood oxygenation, pulse, heart rate variability, blood pressure, respiratory rate, depth of anesthesia and/or hypo- and hypervolemia.

3. The device according to claim 1, wherein the sensor is a video camera.

4. The device according to claim 1, wherein the at least one processor is further programmed to:
    extract the at least one first signal from the measurement readings based on the at least one identified body part.

5. The device according to claim 4, wherein at least one processor is further programmed to:
    estimate motions of the at least one identified body part; and
    extract the at least one first signal in accordance with the estimated motions.

6. The device according to claim 4, wherein the at least one processor is further programmed to:

compare at least two first signals representing component representatives of the physical phenomenon from different body parts of the living being.

7. The device according to claim 6, wherein the at least one processor is further programmed to:
determine a difference between the at least two first signals and for generating a reporting signal if the difference exceeds a threshold.

8. The device according to claim 4, wherein the at least one processor is further programmed to:
generate the output signal based on at least two first signals.

9. The device according to claim 8, wherein the at least one processor is further programmed to:
determine a quality of the at least two first signals; and
select at least one first signal based on the quality.

10. The device according to claim 8, wherein the at least one processor is further programmed to:
merge the at least two first signals for generating the output signal.

11. A processor for processing measurement readings including at least a component representative of a physical phenomenon in a living being, comprising:
an interface for receiving measurement readings from at least one body part of a living being obtained from a distance and having at least a component representative of the physical phenomenon in the living being;
wherein the processor is programmed to:
identify the at least one body part of the living being;
extract at least one first signal from the measurement readings representing at least one component representative of the physical phenomenon;
obtain a calibration curve corresponding to the at least one identified body part; and
adjust the at least one first signal by adjusting first signal values of the at least one first signal to corresponding calibration values of the calibration curve; and
process the calibration curve and the adjusted at least one first signal with the adjusted first signal value to generate at least one output signal representing the physical phenomenon of the living being.

12. A method for processing measurement readings including at least a component representative of a physical phenomenon in a living being, comprising:
with an interface, receiving measurement readings from at least one body part of a living being, the measurement reading including at least a component representative of the physical phenomenon in the living being;
with at least one processor, identifying the at least one body part;
with the at least one processor, extracting at least one first signal from the measurement readings representing at least one component representative of the physical phenomenon;
with the at least one processor, obtaining a calibration curve according to the at least one identified body part;
with the at least one processor, adjusting the at least one first signal by adjusting first signal values of the at least one first signal to corresponding calibration values of the calibration curve;
with the at least one processor, generating at least one output signal representing the physical phenomenon; and
with the at least one processor, controlling a display device to display the output signal representing the physical phenomenon.

13. A non-transitory computer-readable medium comprising program code means for causing a computer to carry out the steps of the method as claimed in claim 12 when said computer program is carried out on the computer.

14. A device for obtaining and processing measurement readings including at least a component representative of a physical phenomenon in a living being, the device comprising:
a camera configured to obtain images of at least one body part of a living being from a distance, the images including measurement readings of the at least one body part having at least a component representative of the physical phenomenon in the living being;
at least one processor programmed to:
identify the at least one body part from the images;
extract at least one first signal from the measurement readings representing the physical phenomenon;
retrieve, from a data storage, at least one predetermined calibration curve based on the at least one identified body part; and
adjust the at least one first signal by adjusting first signal values of the at least one first signal to corresponding calibration values of the at least one calibration curve; and
process the calibration curve and the adjusted at least one first signal with the adjusted first signal value to generate at least one output signal representing the physical phenomenon; and
a display component configured to display the at least one output signal.

15. The device according to claim 14, wherein the physical phenomenon includes motion and the at least one processor is further programmed to:
estimate motions of the at least one identified body part; and
extract the at least one first signal based on the estimated motions.

16. The device according to claim 14, wherein the at least one processor is further programmed to:
determine a difference between at least two first signals representing component representatives of the physical phenomenon; and
generating a reporting signal reporting the physical phenomenon in response to an occurrence of the physical phenomenon.

17. The device according to claim 14, wherein the at least one processor is further programmed to generate the output signal based on at least two first signals.

18. The device according to claim 14, wherein the at least one processor is further programmed to:
determine a quality of the at least two first signals and for selecting at least one first signal based on the quality; and
merge the at least two first signals for generating the output signal.

19. The processor according to claim 11, wherein the physical phenomenon includes motion and the processor is further programmed to:
estimate motions of the at least one identified body part; and
extract the at least one first signal based on the estimated motions.

20. The processor according to claim 11, further programmed to:
determine a difference between at least two first signals representing component representatives of the physical phenomenon; and generating a reporting signal reporting the physical phenomenon in response to an occurrence of the physical phenomenon.

21. The method according to claim 12, further including:

with a sensor, obtaining the measurement readings from a distance; and with a display component, display the at least one output signal.

\* \* \* \* \*